United States Patent [19]

Spada et al.

[11] Patent Number: 5,409,930
[45] Date of Patent: Apr. 25, 1995

[54] BIS MONO- AND BICYCLIC ARYL AND HETEROARYL COMPOUNDS WHICH INHIBIT EGF AND/OR PDGF RECEPTOR TYROSINE KINASE

[75] Inventors: Alfred P. Spada, Lansdale; Martin P. Maquire; Paul E. Persons, both of King of Prussia; Michael R. Myers, Reading, all of Pa.

[73] Assignee: Rhone-Poulenc Rorer Pharmaceuticals Inc., Collegeville, Pa.

[21] Appl. No.: 146,072

[22] PCT Filed: May 6, 1992

[86] PCT No.: PCT/US92/03736
§ 371 Date: Nov. 8, 1993
§ 102(e) Date: Nov. 8, 1993

[87] PCT Pub. No.: WO92/20642
PCT Pub. Date: Nov. 26, 1992

Related U.S. Application Data

[63] Continuation of Ser. No. 698,420, May 10, 1991, abandoned.

[51] Int. Cl.[6] .............. A61K 31/495; A01N 43/58
[52] U.S. Cl. .................... 514/248; 514/314; 544/353; 544/354; 544/355; 546/167
[58] Field of Search ............ 544/354, 355, 353; 546/167; 514/249, 314, 311, 313

[56] References Cited

U.S. PATENT DOCUMENTS

| | | | |
|---|---|---|---|
| 4,322,420 | 3/1982 | Kabayoshi et al. | 424/251 |
| 4,464,375 | 8/1984 | Kabayoshi et al. | 424/251 |
| 4,465,686 | 8/1984 | Lesher et al. | 424/263 |
| 4,599,423 | 7/1986 | Lesher et al. | 546/300 |
| 4,661,499 | 4/1987 | Young et al. | 514/311 |

FOREIGN PATENT DOCUMENTS

| | | |
|---|---|---|
| 0520722 | 12/1992 | European Pat. Off. |
| 1543560 | 4/1979 | United Kingdom |
| 20642 | 11/1992 | WIPO |

*Primary Examiner*—Werren B. Lone
*Attorney, Agent, or Firm*—James A. Nicholsen; Martin F. Savitzky; Raymond S. Parker, III

[57] ABSTRACT

This invention relates to bis mono- and/or bicyclic aryl and/or heteroaryl compounds exhibiting protein tyrosine kinase inhibition activity. More specifically, it relates to the method of inhibiting abnormal cell proliferation in a patient suffering from a disorder characterized by such proliferation comprising the administration thereto of an EGF and/or PDGF receptor inhibiting effective amount of said bis mono- and/or bicyclic aryl and/or heteroaryl compound and to the preparation of said compounds and their use in pharmaceutical compositions used in this method.

13 Claims, No Drawings

BIS MONO- AND BICYCLIC ARYL AND HETEROARYL COMPOUNDS WHICH INHIBIT EGF AND/OR PDGF RECEPTOR TYROSINE KINASE

This application is a 371 of PCT/US 92/03736, May 6, 1992 and a Continuation of 07/698,420, May 10, 1991, abandoned.

FIELD OF THE INVENTION

This invention relates to the inhibition of cell proliferation. More specifically, this invention relates to the use of bis mono- and/or bicyclic aryl and/or heteroaryl compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factor receptors are imbedded in and penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many disease states are characterized by the uncontrolled reproduction of cells. These disease states involve a variety of cell types and include disorders such as leukemia, cancer, psoriasis, inflammatory diseases, bone diseases, atherosclerosis and restenosis occuring subsequent to angioplastic procedures. The inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptor's biological activity. This is not particularly desirable because insulin is needed by the body to perform other biological functions which are not related to cell proliferation. Accordingly, compounds which inhibit the PTK portion of the EGF and/or PDGF receptor at concentrations less than the concentrations needed to inhibit the PTK portion of the insulin receptor could provide valuable agents for selective treatment of cell proliferation disorders.

REPORTED DEVELOPMENTS

It has been reported that the most potent inhibitors of EGF receptors inhibit EGF-induced proliferation of A431/clone 15 cells with little or no effect on the proliferation of such cells when induced by other growth factors. It has been reported also that erbstatin inhibits the autophosphorylation of the EGF receptor in membranes of A431 cells. Higher concentrations of erbstatin are required to inhibit cyclic adenosine 3',5'-monophosphate (cAMP)-dependent protein kinase.

SUMMARY OF THE INVENTION

In accordance with the present invention, there is provided a method of inhibiting abnormal cell proliferation in a patient suffering from a disorder characterized by such proliferation comprising the administration to a patient of an EGF and/or PDGF receptor inhibiting effective amount of a bis mono- and/or bicyclic aryl and/or heteroaryl compound exhibiting protein tyrosine kinase inhibition activity wherein each aryl and/or heteroaryl group is a ring system containing 0–4 hetero atoms, said compound being optionally substituted or polysubstituted.

Another aspect of the present invention relates to pharmaceutical compositions comprising, in admixture with a pharmaceutically acceptable carrier, a pharmaceutically effective amount of a novel compound of the aforementioned type. Another aspect of this invention comprises novel compounds useful in the practice of the present method.

With respect to the method aspects of this invention, the compounds described by Formula I below constitute a class of the aforementioned bis mono- and/or bicyclic aryl, heteroaryl, carbocyclic or heterocarbocyclic compounds for use in the practice of the present invention:

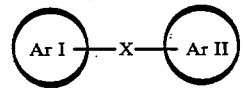

Formula I where:

Ar I and Ar II are independently a substituted or unsubstituted mono-or bicyclic ring, said rings optionally substituted with 0 to about 3 R groups; and X is $(CHR_1)_{0-4}$ or $(CHR_1)_m$—Z—$(CHR_1)_n$ where Z is O, NR', S, SO or $SO_2$, m and n are 0–3 and m+n=0–3 and $R_1$ and R' are independently hydrogen or alkyl; or a pharmaceutically acceptable salt thereof.

Preferably, Ar I is a substituted or unsubstituted mono- or bicyclic aryl or heteroaryl ring system of about 5 to about 12 atoms and where each monocyclic ring may contain 0 to about 3 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.;

Ar II may be as described for Ar I or it may also be saturated carbocyclic wherein said ring comprises either a substituted or unsubstituted monocyclic ring containing 0 to about 2 hetero atoms, or a bicyclic ring containing 0 to about 4 hetero atoms; or a pharmaceutically acceptable salt thereof.

Preferred monocyclic rings include aryl carbocyclic and heterocyclic rings. Exemplary rings are substituted or unsubstituted cyclopentane, cyclohexane, cycloheptane, cyclopent-1-enyl, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, s-triazine, benzene, oxazole and tetrazole.

Further Ar II monocyclic rings include substituted and unsubstituted cycloalkyl and preferably cyclopentyl, cyclohexyl and cycloheptyl.

Preferred bicyclic ring systems include bicyclic aryl, carbocyclic and heterocyclic rings. Exemplary bicyclic rings include substituted and unsubstituted benzofuran, benzothiophene, indole, 1H-indazole, indoline, benzopyrazole, 1,3-benzodioxole, benzoxazole, purine, naphthalene, tetralin, coumarin, chromone, quinoline, isoquinoline, benzimidazole, quinazoline, pyrido[2,3-b]pyrazine, pyrido[3,2-c]pyridazine, pyrido[3,4-b]-pyridine, 2(1H)-quinolone, 1(2H)-isoquinolone, 1,4-benzisoxazine, naphthyridine, benzothiazole, quinoxaline, quinoline-N-oxide, isoquinoline-N-oxide, quinoxaline-N-oxide, quinazoline-N-oxide, benzoxazine, phthalazine, or cinnoline.

Preferred R substitution besides hydrogen independently includes alkyl, alkenyl, phenyl, aralkyl, aralkenyl, hydroxy, alkoxy, aralkoxy, acyloxy, halo, haloalkyl, amino, mono-and di-alkylamino, acylamino, carboxy, carbalkoxy, carbaralkoxy, carbalkoxyalkyl, carbalkoxyalkenyl, amido, mono- and dialkylamido and N,N-cycloalkylamido; and R and R together may also be keto.

Preferred X moieties are $(CHR_1)_{0-2}$, $CH_2—Z—CH_2$ or $Z-CH_2$, where Z is O, NH or S;

A special embodiment of this invention includes those compounds where one of Ar I or Ar II an azidophenyl moiety.

A further special embodiment of this invention includes those compounds where Ar II is cycloalkyl and preferably cyclopentyl, cyclohexyl and cycloheptyl.

As employed above and throughout this disclosure, the following terms, unless otherwise indicated, shall be understood to have the following meanings:

"Monocyclic aryl" means a carbocyclic and/or heterocyclic aromatic ring. Preferred rings include phenyl, thienyl, pyridyl, 2(1H)-pyridonyl, 4(1H)-pyridonyl, furyl, pyrimidinyl, imidazolyl, thiazolyl, oxazolyl and tetrazolyl.

"Bicyclic aryl" means a bicyclic ring system composed of two fused carbocyclic and/or heterocyclic aromatic rings. Preferred rings include naphthyl, indolyl, benzothienyl, benzofuranyl, quinolinyl, chromonyl, 1(2H)-isoquinolonyl, isoquinolinyl, benzimidazolyl, benzothiazolyl, quinoxalinyl, naphthyridinyl, cinnolinyl, phthalazinyl, and quinazolinyl.

"Alkyl", either alone or with various substituents defined herein, means a saturated aliphatic hydrocarbon, either branched- or straight-chained. Preferred alkyl is "loweralkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group. Preferred alkoxy groups include methoxy, ethoxy, propoxy and butoxy.

"Aryloxy" refers to an aryl-O-group. The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy group is acetoxy and benzyloxy;

"Halo" means a halogen. Preferred halogens include chloride, bromide and fluoride.

The preferred haloalkyl group is trifluoromethyl.

The more preferred compounds of this invention include those compounds of Formula I where Ar I and Ar II are independently phenyl, naphthyl, 2(1H)-pyridonyl, pyridyl, quinolinyl, thienyl, 1(2H)-isoquinolonyl, indolyl, napthyridenyl, benzothiazolyl, quinoxalinyl, benzimidazolyl, quinolinyl-N-oxide, isoquinolinyl-N-oxide, quinazolinyl, quinoxalinyl-N-oxide, quinazolinyl-N-oxide, benzoxazinyl, phthalazinyl, or cinnolinyl; and R is hydrogen, alkyl, alkoxy, hydroxy, halo or trifluoromethyl.

More specifically the compounds described by the following subgeneric formulae Ia–Iq are still more preferred:

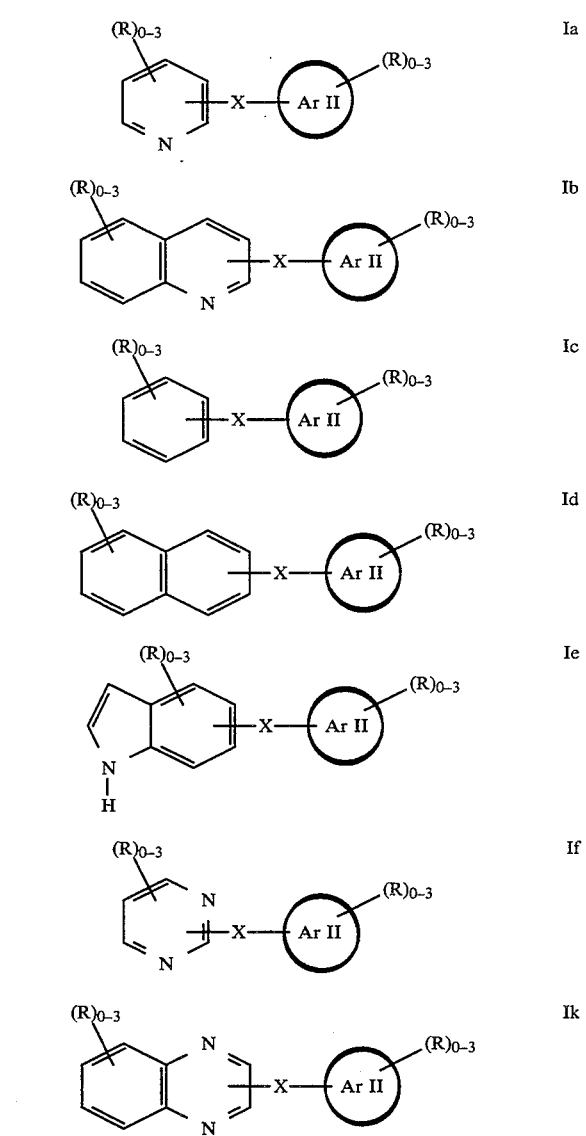

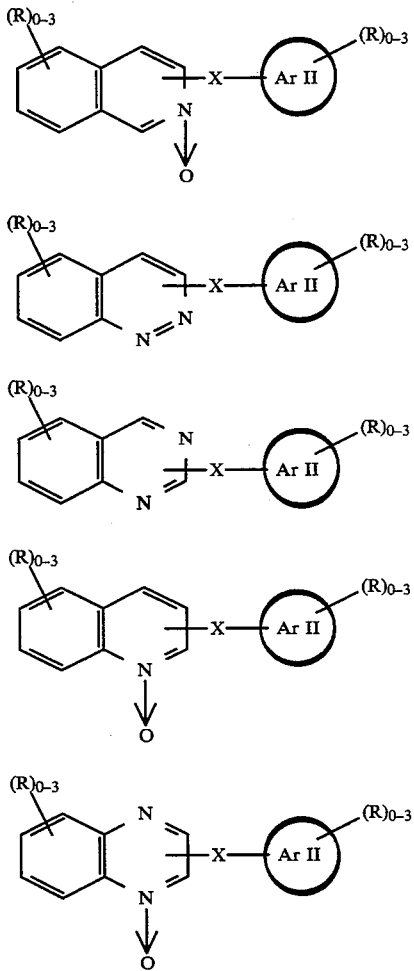

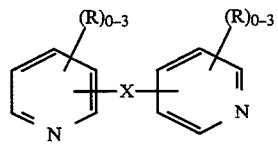

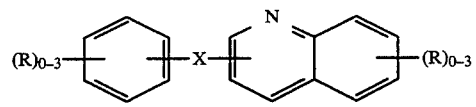

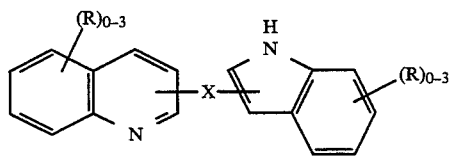

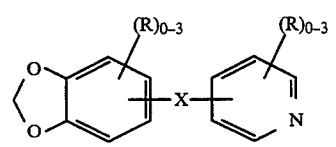

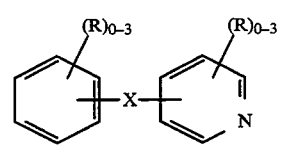

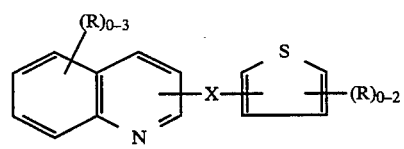

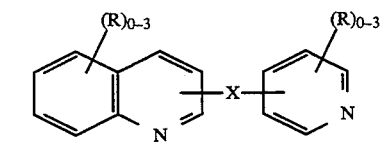

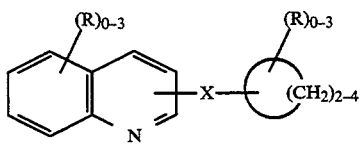

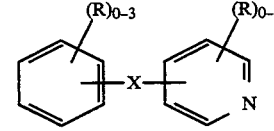

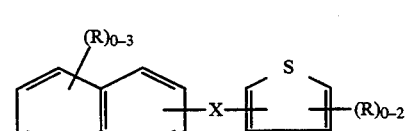

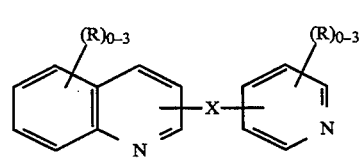

Of course it is to be understood that the R groups which are substituted in the above formulae Ia–Iq are located at any suitable and compatable position of the monocyclic ring or each of the rings of the bicyclic system.

A special embodiment of this invention includes those compounds of the above formulae Ia–Iq where Ar II is thienyl, phenyl, pyridyl, quinolinyl, indolyl, furanyl, imidazolyl, 2(1H)-pyridonyl, 1(2H)-isoquinolonyl and thiazolyl.

A further special embodiment of this invention includes those compounds of formulae Ia–Iq where Ar II is phenyl or thienyl.

Compounds within the scope of this invention inhibit the growth factor induced autophosphorylation of PDGF and/or EGF receptors. It is believed that therapeutically useful PTK inhibiting compounds should not have appreciable activity as inhibitors of serine or threonine kinase systems. In addition these compounds should inhibit growth factor-induced cell proliferation. Compounds meeting these criteria are of considerable value and are particularly useful in the practice of the present invention. Compounds exhibiting selectivity for either of the above receptors are described herein. Certain of these are described by Formulae II–XIX where:

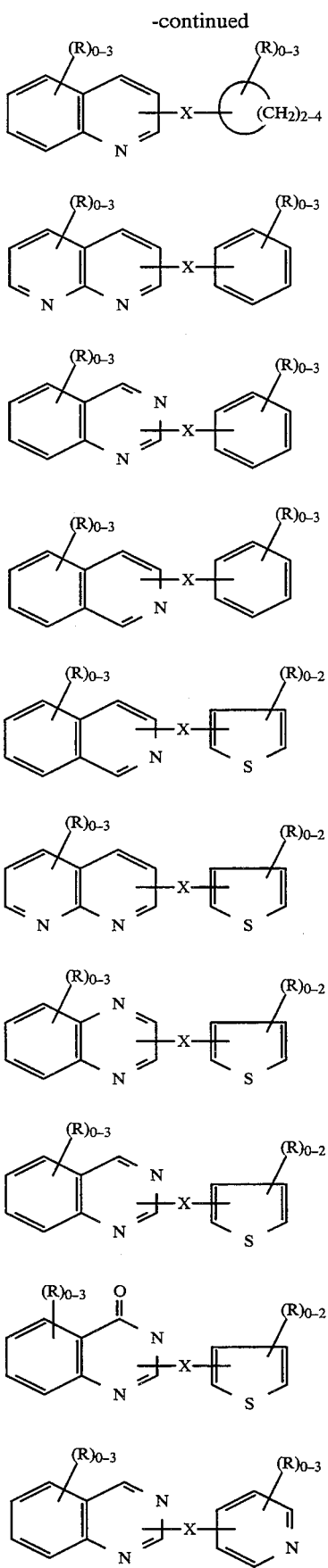

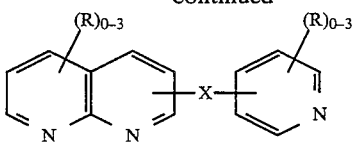

where R is independently hydrogen, loweralkyl, loweralkoxy, hydroxy, halo or trifluoromethyl.

The most preferred compounds are described where the rings are substituted independently by hydrogen, hydroxy, methoxy, ethoxy, chloro, bromo, fluoro or trifluoromethyl.

The compounds of this invention may be useful in the form of the free base, in the form of salts and as a hydrate. All forms are within the scope of the invention. Acid addition salts may be formed and am simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be prepared by employing procedures known in the literature starting from known compounds or readily preparable intermediates. Exemplary general procedures follow.

In general the compounds useful for the method of inhibiting cell proliferation may be prepared by the coupling reaction of a palladium catalyzed aryl or heteroarylstannane with an aryl or heteroarylhalide or triflate.

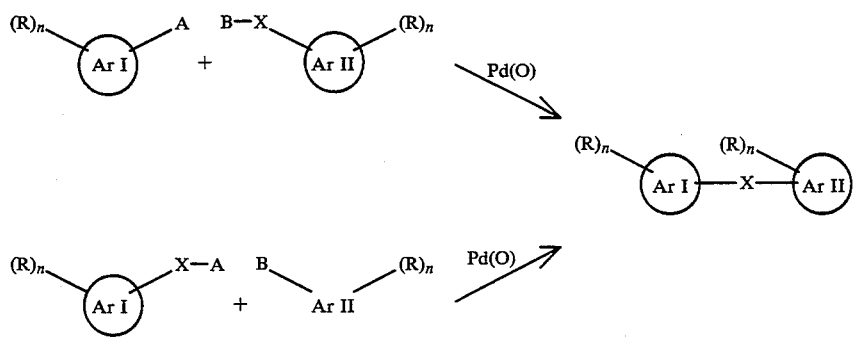

where X is halogen or triflate and Y is trialkylstannane and R and n are as previously described.

Preparation of aryl or heteroaryl substituted quinolines may be prepared as follows.

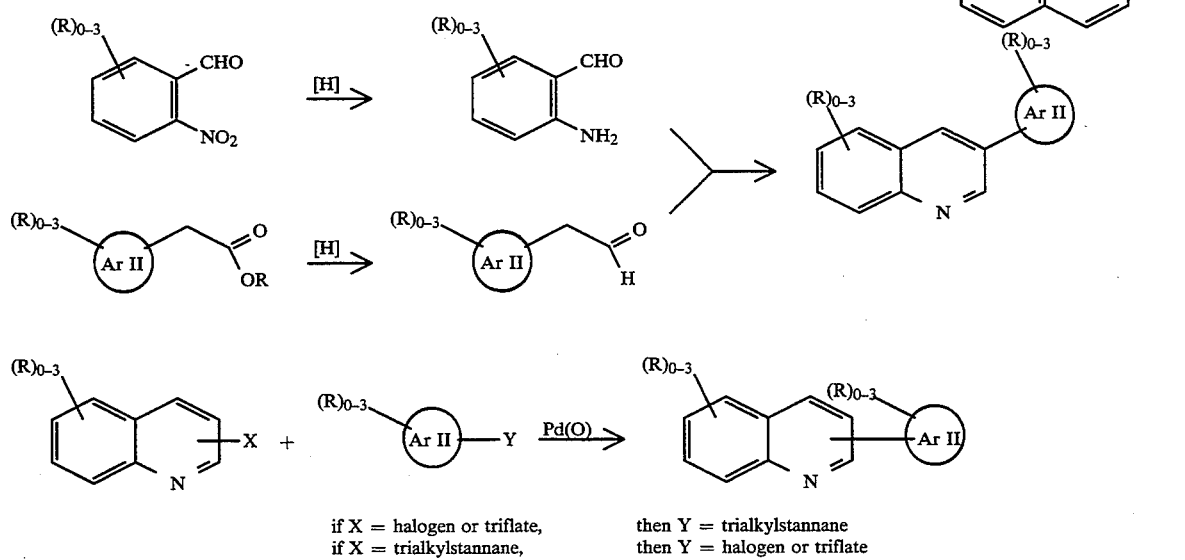

The triflate may be prepared from the corresponding alcohol with triflic anhydride (trifluoromethanesulfonic anhydride) in pyridine

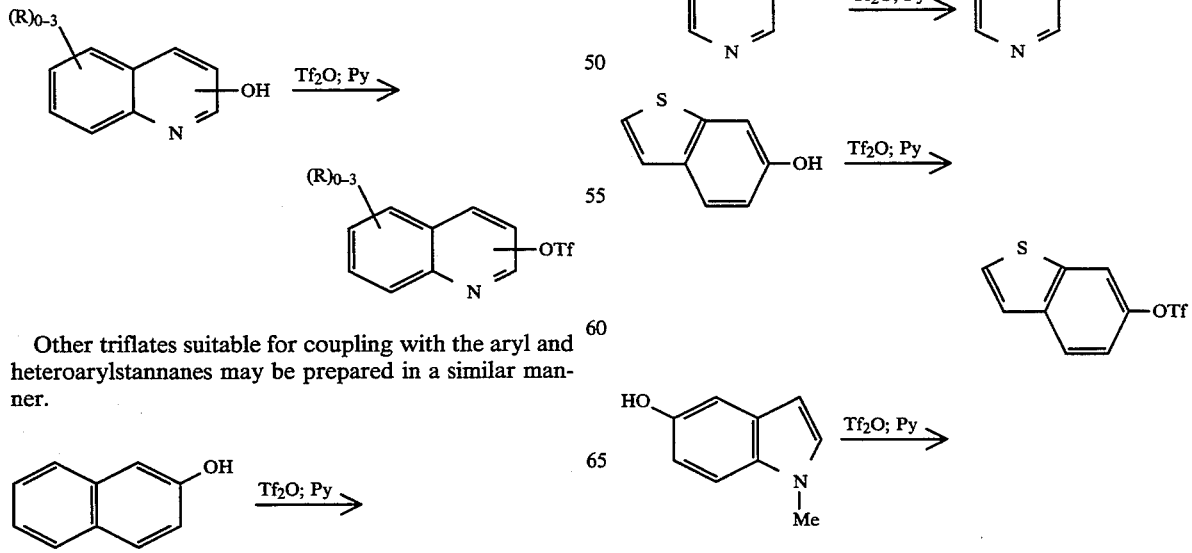

Other triflates suitable for coupling with the aryl and heteroarylstannanes may be prepared in a similar manner.

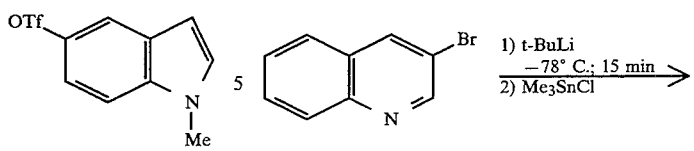

Triflates may also be prepared from 2(1H) or 4(1H) quinolones as shown by the following.

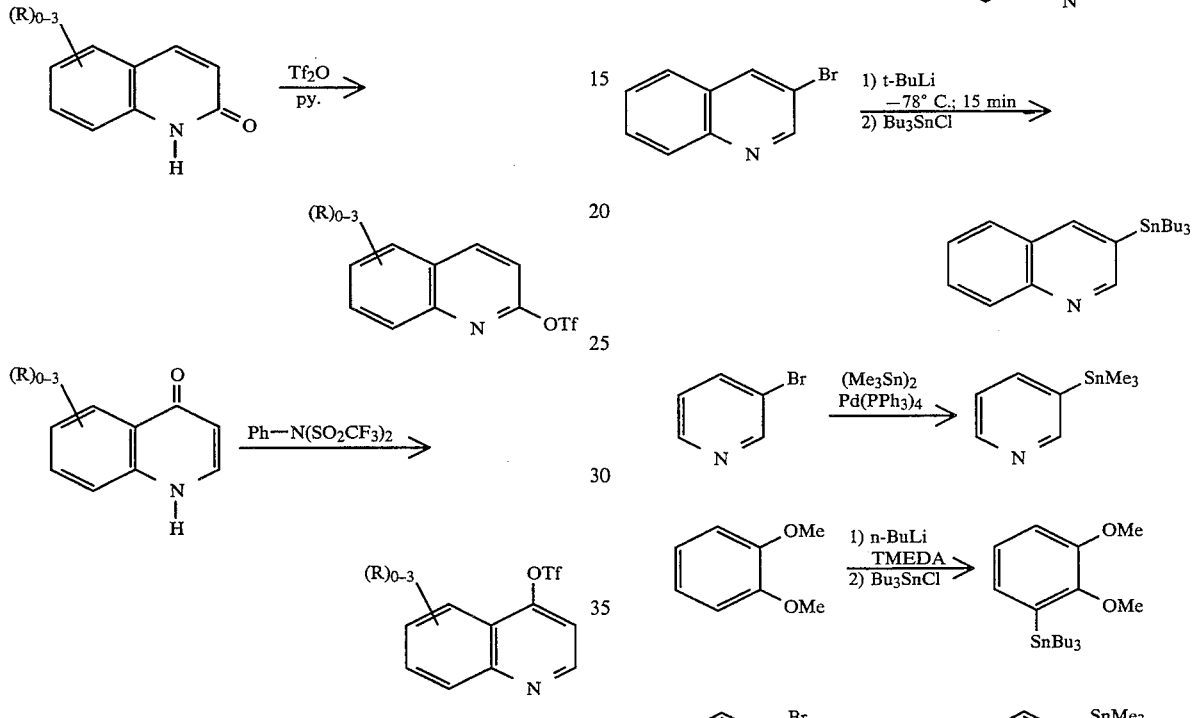

The triflimide such as used in the above reaction may also be used to prepare compounds having a particular substitution such as the following compound.

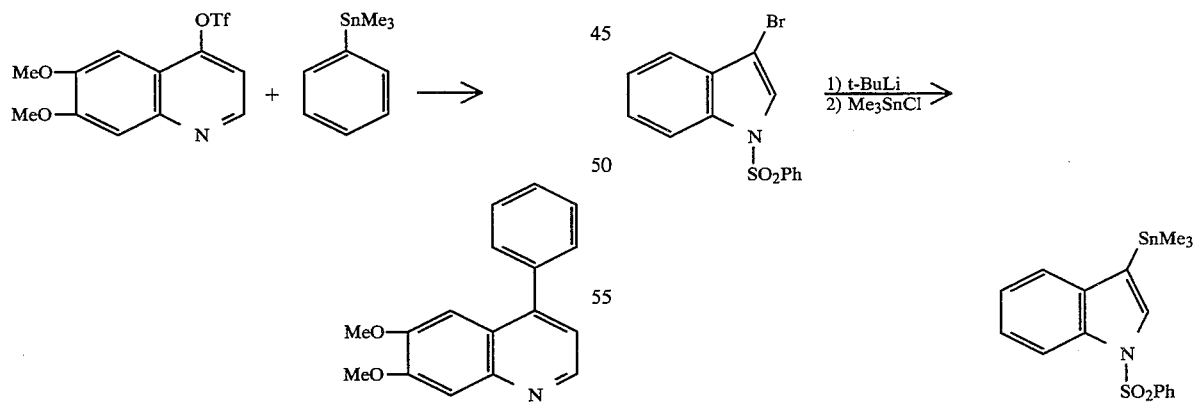

The aryl and heteroarylstannanes may be prepared from the corresponding halide (preferably bromide or iodide) by conversion to the aryllithium (by reaction with t-butyllithium at decreased temperatures, preferably about −78° C.) followed by reaction with a halotrialkylstannane. The following reaction schemes give a representative list of stannanes prepared and the reaction conditions involved.

Further methods which may be employed in the preparation of stannanes of this invention include the following.

(1.) by the action of trimethyltin sodium on aryl halides as described in *Chem. Pharm. Bull.* 1982, 30, 1731–1737:

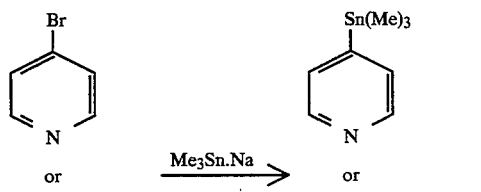

(2.) by heteroatom directed aromatic lithiation process:

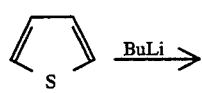

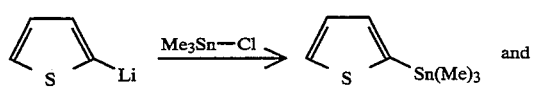 and (3.) by halogen-lithium exchange:

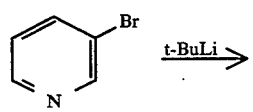

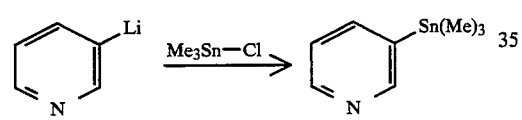

The following are representative coupling reactions which show the preparation of compounds used for the inhibition of cell proliferation

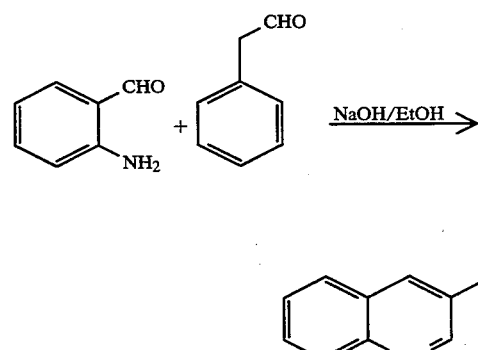

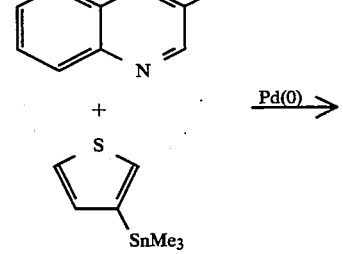

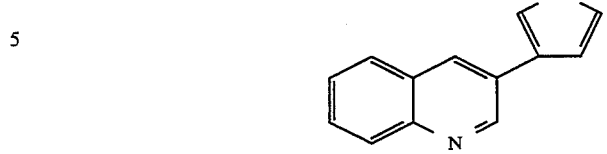

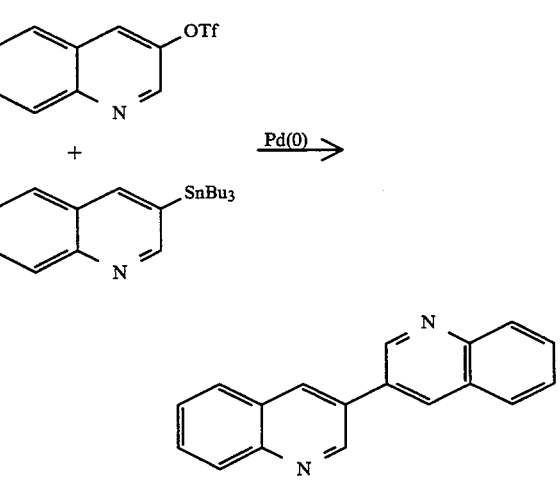

Of course various methods may be employed depending on the reactants involved. Thus, for example, in order to prepare

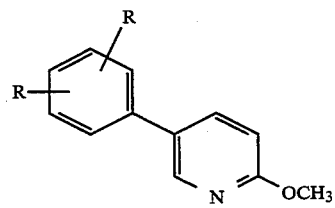

the following methods may be used:

Method A:

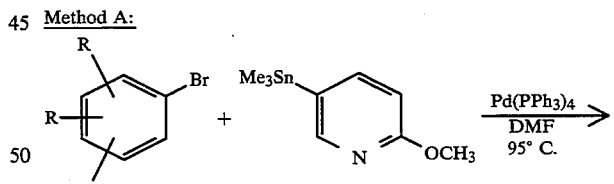

Method B:

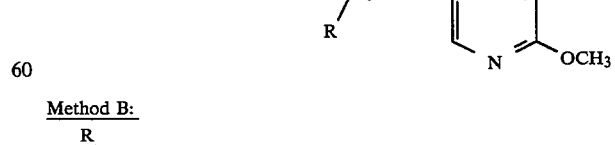

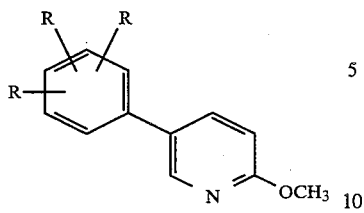

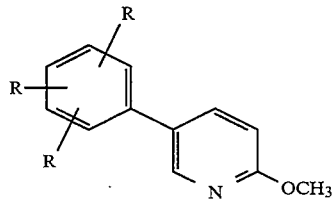

When it is desired that the final product include a 2-(1H) pyridone or 4-(1H) pyridone ring then it is convenient to carry out the condensation on the 2- or 4-alkoxy pyridine followed by selective dealkylation. This can be seen by the following representative scheme.

Method C:

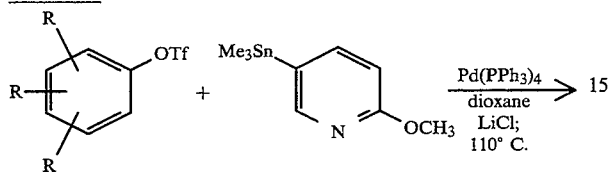

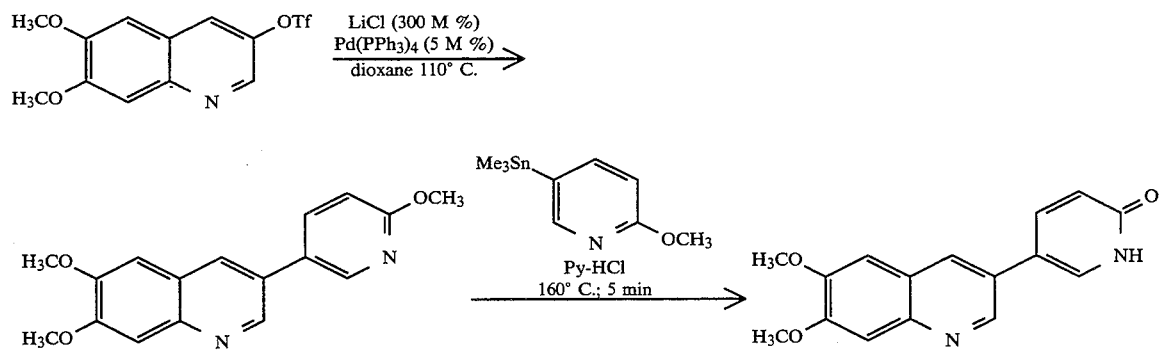

More specifically preparation of aryl or heteroaryl substituted 2(1H)-pyridones may be found in U.S. Pat. Nos. 3,715,358; 3,718,743; 4,465,686 and 4,599,423. Substituted phenyl pyridine preparation may be found in J. Am. Chem. Soc. 111, 877–891 (1989).

Thus it will be a matter of condensing two rings as shown above under the methods described and/or in the art in order to obtain the compounds useful in the practice of inhibition of cell proliferation of this invention. Representative compounds prepared include:
5-(2,4,5-trihydroxyphenyl)-2(1H)-pyridone,
5-(1,4-dihydroxynaphth-2-yl)-2(1H)-pyridone,
5-(2,5-dihydroxyphenyl)-2(1H)-pyridone,
5-(2,5-dihydroxy-4-t-butylphenyl)-2(1H)-pyridone,
3-(2,5-dihydroxyphenyl)-4(1H)-pyridone,
3-(2,5-dihydroxy-4-t-butylphenyl)-4(1 H)-pyridone,
3-(thien-3-yl)-6,7-dimethoxyquinoline,
3-(pyrid-3-yl)indole,
2-(2,5-dihydroxy-4-t-butylphenyl)pyridine and
4-(2,5-dihydroxyphenyl)-1(2H)-isoquinolone.

Method D:

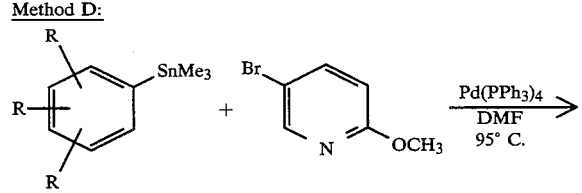

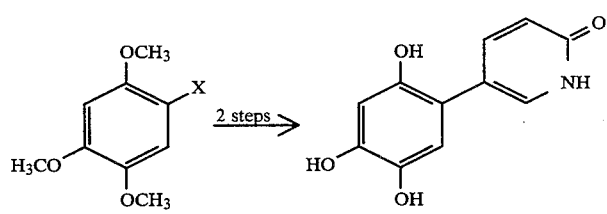

-continued
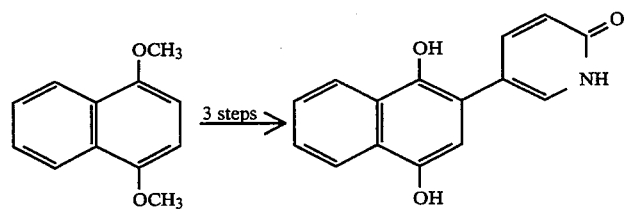
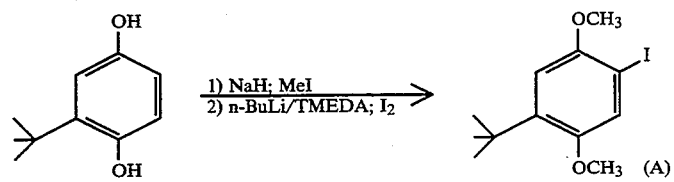
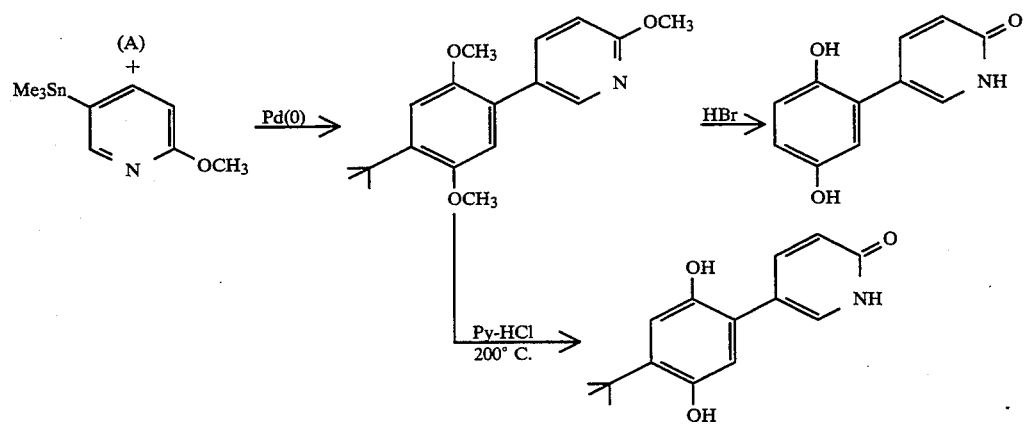
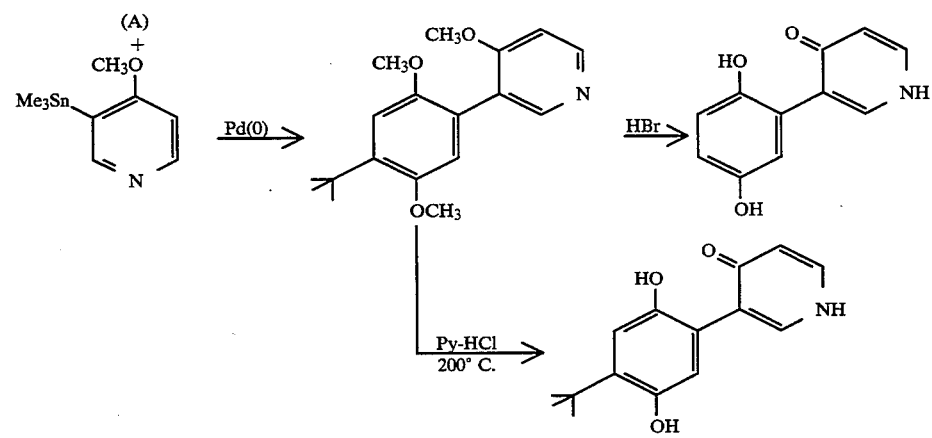
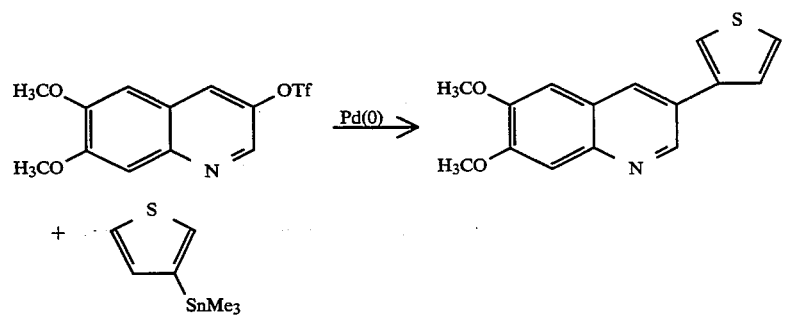

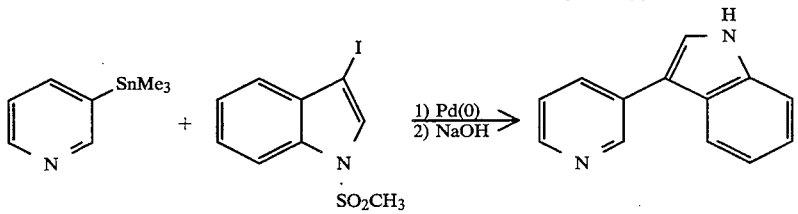

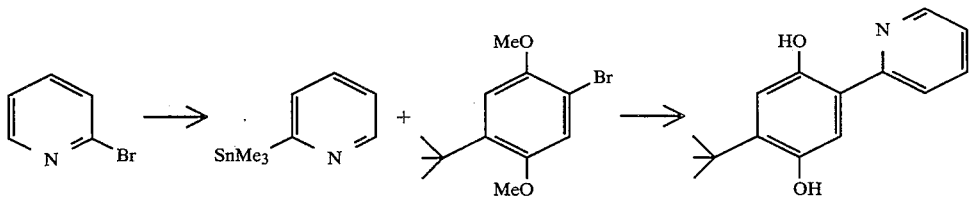

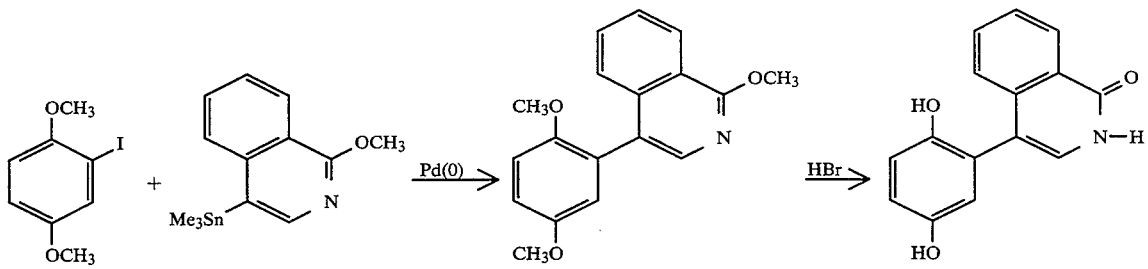

The compounds of the present invention may be prepared by the following representative examples.

EXAMPLE 1

2-methoxy-5-trimethylstannylpyridine

A solution of 1.74 g (9.26 mmol) of 2-methoxy-5-bromopyridine, 3.84 mL (6.07 g; 18.5 mmol) of hexamethylditin and 516 mg (0.446 mmol) of Pd (PPh$_3$)$_4$ in 35 mL of dry toluene is flushed thoroughly with nitrogen and heated to 90° C. for 4 hours. The mixture is then evaporated and chromatographed on silica gel (eluting with hexane and then with 95:5 hexane/ethyl acetate) to give 2-methoxy-5-trimethylstannylpyridine as a colorless oil which is used directly in the next step.

EXAMPLE 2

When the procedure of Example 1 is followed and 2-methoxy-5-bromopyridine is replaced by the compounds of Table I below, then the compounds of Table II below are prepared. (Methods outlined on page 14 may also be used.)

TABLE I 2-methoxyphenyl bromide
3-methoxyphenyl bromide
4-methoxyphenyl bromide
2,3-dimethoxyphenyl bromide
2,4-dimethoxyphenyl bromide
2,5-dimethoxyphenyl bromide
2,6-dimethoxyphenyl bromide
3,4-dimethoxyphenyl bromide
3,5-dimethoxyphenyl bromide
3,4,5-trimethoxyphenyl bromide
2,3,4-trimethoxyphenyl bromide
2,5-dimethoxy-4-t-butylphenyl bromide
2,5-dimethoxy-4-phenylphenyl bromide
2,4-dimethylphenyl bromide
2,5-dimethylphenyl bromide
2-methyl-5-methoxyphenyl bromide
4-chlorophenyl bromide
4-fluorophenyl bromide
2,5-dichlorophenyl bromide
3,4-dichlorophenyl bromide
4-dimethylaminophenyl bromide
4-acetylaminophenyl bromide
4-(N,N-dimethylaminocarbonyl)phenyl bromide
4-t-butoxycarbonylphenyl bromide
4-(pyrrolidinocarbonyl)phenyl bromide
3,5-bis(trifluoromethyl)phenyl bromide
4-bromobiphenyl
2-bromopyridine
3-bromopyridine
4-bromopyridine
2-methoxy-5-bromopyridine
4-methoxy-5-bromopyridine
6-methoxy-5-bromopyridine
2,3-dimethoxy-5-bromopyridine
2,4-dimethoxy-5-bromopyridine
2-acetylamino-5-bromopyridine
2-bromothiophene
3-bromothiophene
2-methoxy-3-bromothiophene
2-methoxy-4-bromothiophene
2-methoxy-5-bromothiophene
3-methoxy-5-bromothiophene
4-methoxy-2-bromothiophene
3-bromofuran
t-butyl 5-bromo-2-furoate
2-bromothiazole
2-bromooxazole
1-methyl-3-bromopyrazole 5-bromopyrimidine
2-bromopyrazine
4-bromopyridazine
1-bromonaphthalene
2-bromonaphthalene
2-bromo-6-methoxynaphthalene
2-bromo-6,7-dimethoxynaphthalene
2-bromoquinoline
3-bromoquinoline
4-bromoquinoline
5-bromoquinoline
6-bromoquinoline
6,7-dimethoxy-3-bromoquinoline
6-methoxy-3-bromoquinoline
7-methoxy-3-bromoquinoline
7,8-dimethoxy-3-bromoquinoline
6,7-dichloro-3-bromoquinoline
4-bromoisoquinoline
3-bromoisoquinoline
1-bromoisoquinoline
6,7-dimethoxy-3-bromoisoquinoline
N-methanesulfonyl-3-bromoindole
N-methanesulfonyl-5-bromoindole
N-methanesulfonyl-3-bromo-5-methoxyindole
N-methanesulfonyl-3-bromo-5-chloroindole
2-bromobenzothiophene
3-bromobenzothiophene
8-bromopurine
7-methyl-2-bromopurine
3-bromopyrido-[3,4-b]-pyridine

TABLE II 2-methoxyphenyl trimethylstannane
3-methoxyphenyl trimethylstannane
4-methoxyphenyl trimethylstannane
2,3-dimethoxyphenyl trimethylstannane
2,4-dimethoxyphenyl trimethylstannane
2,5-dimethoxyphenyl trimethylstannane
2,6-dimethoxyphenyl trimethylstannane
3,4-dimethoxyphenyl trimethylstannane
3,5-dimethoxyphenyl trimethylstannane
3,4,5-trimethoxyphenyl trimethylstannane
2,3,4-trimethoxyphenyl trimethylstannane
2,5-dimethoxy-4-t-butylphenyl trimethylstannane
2,5-dimethoxy-4-phenylphenyl trimethylstannane
2,4-dimethylphenyl trimethylstannane
2,5-dimethylphenyl trimethylstannane
2-methyl-5-methoxyphenyl trimethylstannane
4-chlorophenyl trimethylstannane
4-fluorophenyl trimethylstannane
2,5-dichlorophenyl trimethylstannane
3,4-dichlorophenyl trimethylstannane
4-dimethylaminophenyl trimethylstannane
4-acetylaminophenyl trimethylstannane
4-(N,N-dimethylaminocarbonyl)phenyl trimethylstannane
4-t-butoxycarbonylphenyl trimethylstannane
4-(pyrrolidinocarbonyl)phenyl trimethylstannane
3,5-bis(trifluoromethyl)phenyl trimethylstannane
4-trimethylstannylbiphenyl
2-trimethylstannylpyridine
3-trimethylstannylpyridine
4-trimethylstannylpyridine
2-methoxy-5-trimethylstannylpyridine
4-methoxy-5-trimethylstannylpyridine
6-methoxy-5-trimethylstannylpyridine
2,3-dimethoxy-5-trimethylstannylpyridine
2,4-dimethoxy-5-trimethylstannylpyridine
2-acetylamino-5-trimethylstannylpyridine
2-trimethylstannylthiophene
3-trimethylstannylthiophene
2-methoxy-3-trimethylstannylthiophene
2-methoxy-4-trimethylstannylthiophene
2-methoxy-5-trimethylstannylthiophene
3-methoxy-5-trimethylstannylthiophene
4-methoxy-2-trimethylstannylthiophene
3-trimethylstannylfuran
t-butyl 5-trimethylstannyl-2-furoate
2-trimethylstannylthiazole
2-trimethylstannyloxazole
1-methyl-3-trimethylstannylpyrazole
5-trimethylstannylpyrimidine
2-trimethylstannylpyrazine
4-trimethylstannylpyridazine
1-trimethylstannylnaphthalene
2-trimethylstannylnaphthalene
2-trimethylstannyl-6-methoxynaphthalene
2-trimethylstannyl-6,7-dimethoxynaphthalene
2-trimethylstannylquinoline
3-trimethylstannylquinoline
4-trimethylstannylquinoline
5-trimethylstannylquinoline
6-trimethylstannylquinoline
6,7-dimethoxy-3-trimethylstannylquinoline
6-methoxy-3-trimethylstannylquinoline
7-methoxy-3-trimethylstannylquinoline
7,8-dimethoxy-3-trimethylstannylquinoline
6,7-dichloro-3-trimethylstannylquinoline
4-trimethylstannylisoquinoline
3-trimethylstannylisoquinoline
1-trimethylstannylisoquinoline
6,7-dimethoxy-3-trimethylstannylisoquinoline
N-methanesulfonyl-3-trimethylstannylindole
N-methanesulfonyl-5-trimethylstannylindole
N-methanesulfonyl-3-trimethylstannyl-5-methoxyindole
N-methanesulfonyl-3-trimethylstannyl-5-chloroindole
2-trimethylstannylbenzothiophene
3-trimethylstannylbenzothiophene
8-trimethylstannylpurine
7-methyl-2-trimethylstannylpurine
3-trimethylstannylpyrido-[3,4-b]-pyridine

EXAMPLE 3

6,7-dimethoxyquinolin-3-yl trifluoromethanesulfonate

A solution of 1.84 g (8.98 mmol) of 3-hydroxy-6,7-dimethoxyquinoline in 22 mL of dry pyridine is cooled to 0° C. and 3.20 mL (5.38 g; 19.1 mmol) of trifluoromethanesulfonic anhydride is added via syringe. The solution is allowed to warm to 22° C. and stirred for 4 hours. The solution is then partitioned between ethyl acetate (150 mL) and water (100 mL). The aqueous layer is back extracted with ethyl acetate (100 mL) and the combined organics dried (Na$_2$SO$_4$) and evaporated. The resulting residue is chromatographed on silica gel (eluting with chloroform) to give a white solid which is recrystallized from hexane to give 6,7-dimethoxyquinolin-3-yl trifluoromethanesulfonate. (mp 82.5°–84° C.)

EXAMPLE 4

When the procedure of Example 3 is followed and 3-hydroxy-6,7-dimethoxyquinoline is replaced by the compounds of Table III below, then the products of Table IV are prepared

TABLE III phenol
2-methoxyphenol
3-methoxyphenol
4-methoxyphenol
2,3-dimethoxyphenol
3,4-dimethoxyphenol
3,5-dimethoxyphenol
3,4,5-trimethoxyphenol
2-chlorophenol
3-chlorophenol
4-chlorophenol
4-bromophenol
2,4-dichlorophenol
2,5-dichlorophenol
3,5-dichlorophenol
3,5-bis(trifluoromethyl)phenol
3-dimethylaminophenol
o-cresol
m-cresol
p-cresol
α,α,α-trifluoro-p-cresol
3-ethylphenol
4-tert-butylphenol
2,4-dimethylphenol
2,5-dimethylphenol
3,4-dimethylphenol
4-benzyloxyphenol
2-phenylphenol
4-phenylphenol
2,3,5-trimethyphenol
4-nitrophenol
4-acetylaminophenol
2-bromo-4-methylphenol
3'-hydroxyacetophenone
4'-hydroxyacetophenone
methyl 3-hydroxybenzoate
methyl 4-hydroxy-3-methoxybenzoate
N,N-dimethyl-4-hydroxybenzamide
1-naphthol
2-naphthol
6-methoxy-1-naphthol
6-methoxy-2-naphthol
6,7-dimethoxy-1-naphthol
6,7-dimethoxy-2-naphthol
5,8-dimethoxy-2-naphthol
6-bromo-2-naphthol
2-hydroxyquinoline
2-hydroxy-4-methylquinoline
6,7-dimethoxy-2-hydroxyquinoline
3-hydroxyquinoline
4-hydroxyquinoline
6,7-dimethoxy-4-hydroxyquinoline
7-chloro-4-hydroxyquinoline
1-hydroxyisoquinoline
5-hydroxyisoquinoline
2-hydroxypyridine
3-hydroxypyridine
4-hydroxypyridine
2,3-dimethoxy-5-hydroxypyridine
5-chloro-2-pyridinol
5-chloro-3-pyridinol
3-hydroxypicolinamide

TABLE IV phenyl trifluoromethane sulfonate
2-methoxyphenyl trifluoromethane sulfonate
3-methoxyphenyl trifluoromethane sulfonate
4-methoxyphenyl trifluoromethane sulfonate
2,3-dimethoxyphenyl trifluoromethane sulfonate
3,4-dimethoxyphenyl trifluoromethane sulfonate
3,5-dimethoxyphenyl trifluoromethane sulfonate
3,4,5-trimethoxyphenyl trifluoromethane sulfonate
2-chlorophenyl trifluoromethane sulfonate
3-chlorophenyl trifluoromethane sulfonate
4-chlorophenyl trifluoromethane sulfonate
4-bromophenyl trifluoromethane sulfonate
2,4-dichlorophenyl trifluoromethane sulfonate
2,5-dichlorophenyl trifluoromethane sulfonate
3,5-dichlorophenyl trifluoromethane sulfonate
3,5-bis(trifluoromethyl)phenyl trifluoromethane sulfonate
3-dimethylaminophenyl trifluoromethane sulfonate
o-cresyl trifluoromethane sulfonate
m-cresyl trifluoromethane sulfonate
p-cresyl trifluoromethane sulfonate
a,a,a-trifluoro-p-cresyl trifluoromethane sulfonate
3-ethylphenyl trifluoromethane sulfonate
4-tert-butylphenyl trifluoromethane sulfonate
2,4-dimethylphenyl trifluoromethane sulfonate
2,5-dimethylphenyl trifluoromethane sulfonate
3,4-dimethylphenyl trifluoromethane sulfonate
4-benzyloxyphenyl trifluoromethane sulfonate
2-phenylphenyl trifluoromethane sulfonate
4-phenylphenyl trifluoromethane sulfonate
2,3,5-trimethyphenyl trifluoromethane sulfonate
4-nitrophenyl trifluoromethane sulfonate
4-acetamidophenyl trifluoromethane sulfonate
2-bromo-4-methylphenyl trifluoromethane sulfonate
3-acetylphenyl trifluoromethane sulfonate
4-acetylphenyl trifluoromethane sulfonate
3-methoxycarbonylphenyl trifluoromethane sulfonate
2-methoxy-4-methoxycarbonylphenyl trifluoromethane sulfonate
4-N,N-dimethylaminocarbonylphenyl trifluoromethane sulfonate
naphth-1-yl trifluoromethane sulfonate
naphth-2-yl trifluoromethane sulfonate
6-methoxynaphth-1-yl trifluoromethane sulfonate
6-methoxynaphth-2-yl trifluoromethane sulfonate
6,7-dimethoxynaphth-1-yl trifluoromethane sulfonate
6,7-dimethoxynaphth-2-yl trifluoromethane sulfonate
5,8-dimethoxynaphth-2-yl trifluoromethane sulfonate
6-bromonaphth-2-yl trifluoromethane sulfonate
quinolin-2-yl trifluoromethane sulfonate
4-methylquinolin-2-yl trifluoromethane sulfonate
6,7-dimethoxyquinolin-2-yl trifluoromethane sulfonate
quinolin-2-yl trifluoromethane sulfonate
quinolin-4-yl trifluoromethane sulfonate
6,7-dimethoxyquinolin-4-yl trifluoromethane sulfonate
7-chloroquinolin-4-yl trifluoromethane sulfonate
isoquinolin-1-yl trifluoromethane sulfonate
isoquinolin-5-yl trifluoromethane sulfonate
pyridin-2-yl trifluoromethane sulfonate
pyridin-3-yl trifluoromethane sulfonate
pyridin-4-yl trifluoromethane sulfonate
2,3-dimethoxypyridin-5-yl trifluoromethane sulfonate
5-chloro-2-pyridin-2-yl trifluoromethane sulfonate
5-chloro-3-pyridinyl trifluoromethane sulfonate
picolin-3-amido trifluoromethane sulfonate

EXAMPLE 5

2,5-dimethoxy-4-t-butylphenyl iodide

A stirred solution of 3.00 g (15.5 mmol) of 1,4-dimethoxy-2-t-butylbenzene (obtained by methylation of t-butyl hydroquinone with sodium hydride and methyl iodide in tetrahydrofuran) and 2.52 g (21.7 mmol) of tetramethylethylenediamine in 50 mL of anhydrous ether under nitrogen is cooled to 0° C. and 8.66 mL (21.7 mmol) of n-butyllithium (2.5M in hexane) is added over a 5 minute period. The mixture is warmed to 22° C., stirred for 18 hours and then cooled back to 0° C. The reaction is quenched with 7.86 g (30.9 mmol) of iodine in 30 mL of tetrahydrofuran and partitioned between ethyl acetate (200 mL) and 10% $NaHSO_3$ (300 mL). The organic layer is washed with water (50 mL), brine (50 mL), dried ($MgSO_4$) and evaporated to give a brown, partially crystalline oil which is chromatographed on silica gel (eluting with 98:2 hexane/ethyl acetate) to give crude product which is recrystallized from hexane to obtain 2,5-dimethoxy-4-t-butylphenyl iodide (mp 80.5°–82.5° C.)

EXAMPLE 6

When the procedure of Example 5 is followed and the appropriate starting material is used, the following compounds of Table V may be prepared.

TABLE V 2,3-dimethoxyphenyl iodide
2,3,4-trimethoxyphenyl iodide
2,4-dimethoxy-3-t-butylphenyl iodide
4-iodo-1,3-benzodioxole

EXAMPLE 7

5-(3,4-dimethoxyphenyl)-2-methoxypyridine

A solution of 2.00 g (6.64 mmol) of 4-trimethylstannylveratrole, 2.49 g (13.2 mmol) of 2-methoxy-5-bromopyridine and 370 mg (0.332 mmol) of Pd($PPh_3$)$_4$ in 30 mL of dry dimethylformamide is flushed thoroughly with nitrogen and heated to 90° C. for 12 hours. The reaction mixture is partitioned between ethyl acetate (150 mL) and water (100 mL). The aqueous layer is back extracted with ethyl acetate (100 mL) and the combined organics are washed with brine (75 mL), dried ($MgSO_4$) and evaporated to give a crude yellow oil. The oil is chromatographed on silica gel (eluting with 95:5 hexane/ethyl acetate and then with 9:1 hexane/ethyl acetate) which gives 5-(3,4-dimethoxyphenyl)-2-methoxypyridine (m.p 83°–84° C.)

EXAMPLE 8

When the procedure of Example 7 is followed and 2-methoxy-5-bromopyridine is replaced with the bromo compounds of Example 2, Table I, then the corresponding products are obtained.

EXAMPLE 9

When the procedure of Example 7 is followed and 4-trimethylstannylveratrole is replaced by the stannanes of Example 2, Table II, then the corresponding products are obtained.

EXAMPLE 10

When the procedure of Example 7 is followed and 2-methoxy-5-bromopyridine is replaced with the bromo compounds of Example 2, Table I and 4-trimethylstannylveratrole is replaced by the stannanes of Example 2, Table II, then the corresponding products are obtained. A representative list of compounds so prepared are shown below in Table VI.

TABLE VI 2-(2,3,4-trimethoxyphenyl)pyridine
2,3-dimethoxy-6-(thien-3-yl)naphthaylene
3-(2,3-dimethoxyphenyl)quinoline
3-(benzothien-3-yl)quinoline
4-(phenyl)phenyl-1,4-dimethoxybenzene
2-(2,5-dimethoxyphenyl)naphthaylene
5-(2,5-dimethoxyphenyl)pyrimidine
5-phenyl-1,2,4-trimethoxybenzene
2-methoxy-5-(2,3,5-trimethoxyphenyl)pyridine
2-methoxy-5-(1,4-dimethoxynaphth-2-yl)pyridine
3-(2,5-dimethoxyphenyl)thiophene
2-methoxy-5-(2,5-dimethoxy-4-phenyl)phenylpyridine
3,6-dihydroxy-4-phenylveratrole
4-(2,5-dimethoxyphenyl)veratrole

EXAMPLE 11

3-(2-methoxypyrid-5-yl)-6,7-dimethoxyquinoline

A mixture of 800 mg (2.94 mmol) of 2-methoxy-5-trimethylstannylpyridine, 994 mg (2.94 mmol) of 6,7-dimethoxyquinolin-3-yl trifluoromethane sulfonate, 374 mg (8.82 mmol) of anhydrous lithium chloride and 170 mg (0.147 mmol) of Pd($PPh_3$)$_4$ in 15 mL of anhydrous dioxane is flushed thoroughly with nitrogen and refluxed for 6 hours. The mixture is diluted with ethyl acetate (100 mL), washed with saturated $NaHCO_3$ (75 mL), dried ($Na_2SO_4$) and evaporated. The resulting residue is chromatographed on silica gel (eluting with chloroform) to give a solid material which is recrystallized from ethyl acetate to give 3-(2-methoxypyrid-5-yl)-6,7-dimethoxyquinoline (m.p. 170.5°–171.5° C.).

EXAMPLE 12

When the procedure of Example 11 is followed and 2-methoxy-5-trimethylstannylpyridine is replaced by the stannanes of Example 2, Table II, then the corresponding products are obtained.

EXAMPLE 13

When the procedure of Example 11 is followed and 6,7-dimethoxyquinolin-3-yl trifluoromethane sulfonate is replaced by the triflates of Example 4, Table IV, then the corresponding products are prepared.

EXAMPLE 14

When the procedure of Example 11 is followed and 2-methoxy-5-trimethylstannylpyridine is replaced by the stannanes of Example 2, Table II, and 6,7-dimethoxyquinolin-3-yl trifluoromethane sulfonate is replaced by the triflates of Example 4, Table IV, then the corresponding products are prepared. A representative list of compounds so prepared is shown below in Table VII.

TABLE VII 3-(thien-3-yl)-6,7-dimethoxyquinoline (m.p. 116°–118° C.)
2-methoxy-5-(3,4,5-trimethoxyphenyl)pyridine (m.p. 71°–72° C. )
4-(thien-3-yl)-6,7-dimethoxyquinoline (m. p. 134°–135° C.)
2-(thien-3-yl)-6,7-dimethoxyquinoline (135.5°–138° C.)

3-(quinolin-3-yl)-6,7-dimethoxyquinoline (m. p. 190.5°–191° C.)
3-(thien-3-yl)-6,7-dichloroquinoline (m.p. 167°–167.5° C.)
3-(thien-3-yl)-7-methoxyquinoline (m.p. 122°–124° C.)
3-(3,4-dichlorophenyl)-6,7-dimethoxyquinoline (m. p.184°–186° C.)
3-(4-methoxyphenyl)-6,7-dimethoxyquinoline (m.p. 162.5°–164.5° C.)
3-(naphth-2-yl)-6,7-dimethoxyquinoline (m.p. 162.5°–165° C.)
3-(4-phenyl)phenyl-6,7-dimethoxyquinoline (m.p. 143°–145° C.)
3-(thien-2-yl)-6,7-dimethoxyquinoline (m.p. 122.5°–124° C.)
3-(5-methoxythien-2-yl)-6,7-dimethoxyquinoline (111°–113° C.)
4-phenyl-6,7-dimethoxyquinoline (m.p. 124°–125° C.)
3-(5-chlorothien-2-yl)-6,7-dimethoxyquinoline (131.5°–132° C.)
3-(furan-3-yl)quinoline (m.p. 87°–90° C.)
5-(2,5-dimethoxyphenyl)pyridine (m.p. 92.5°–94.5° C.)
5-(2,5-dimethoxyphenyl)-2-methoxypyridine (oil)

EXAMPLE 15

2-methoxy-5-[(2,5-dimethoxy-4-t-butyl)phenyl]pyridine

When the procedure of Example 7 is followed and 4-trimethylstannylveratrole is replaced with 2-methoxy-5-trimethylstannylpyridine and 2-methoxy-5-bromopyridine is replaced with 2,5-dimethoxy-4-t-butylphenyl iodide from Example 5, then the compound prepared is 2-methoxy-5-[(2,5-dimethoxy-4-t-butyl)-phenyl]pyridine as an oil.

EXAMPLE 16

5-[(2,5-dimethoxy-4-t-butyl)phenyl]pyridine

When 2-methoxy-5-trimethylstannylpyridine in Example 15 is replaced by 5-trimethylstannylpyridine, the compound prepared is 5-[(2,5-dimethoxy-4-t-butyl)-phenyl]pyridine (m.p. 92.5°–94.5° C.).

EXAMPLE 17

5-[(2,5-dihydroxy-4-t-butylphenyl]-2(1H)-pyridone

A mixture of 252 mg (0.837 mmol) of 2-methoxy-5-[(2,5-dimethoxy-4-t-butyl)-phenyl]pyridine and 7.0 g of pyridine hydrochloride is heated to 210° C. for 1 hour, cooled and diluted with 60 mL of water. The mixture is cooled to 0° C., filtered, and recrystallized from methanol to obtain 5-[(2,5-dihydroxy-4-t-butyl)phenyl]-2(1H)-pyridone [m.p. 270°–5° C.(softens) >300° C.(dec)].

EXAMPLE 18

5-[(2,5-dihydroxy-4-t-butyl)phenyl]pyridine

When the procedure of Example 17 is followed and 2-methoxy-5-[(2,5-dimethoxy-4-t-butyl)phenyl]pyridine is replaced by 5-[2,5-dimethoxy-4-t-butyl)phenyl]pyridine, the product obtained is 5-[(2,5-dihydroxy-4-t-butyl)phenyl]pyridine (m.p. 202°–204° C.).

EXAMPLE 19

5-(2,5-dihydroxyphenyl)-2(1H)-pyridone

A solution of 502 mg (2.05 mmol) of 2-methoxy-5-(2,5-dimethoxyphenyl)pyridine in 20 mL of 48% hydrobromic acid (aqueous) is refluxed for 6 hours, cooled to ca. 25° C. and diluted with 150 mL of water. The mixture is neutralized with solid NaHCO3, cooled to 0° C. and the resulting solid product collected by filtration. The solid is washed well with water, collected by centrifugation, then further purified by recrystalization in methanol to obtain 5-(2,5-dihydroxyphenyl)-2(1H)-pyridone (m.p. 303°–306° C. dec).

EXAMPLE 20

When the procedure of Example 19 is followed and 2-methoxy-5-(2,5-dimethoxyphenyl)pyridine is replaced by 2-methoxy-5-(3,4-dimethoxyphenyl)pyridine, 2-methoxy-5-(3,4,5-trimethoxyphenyl)pyridine or 5-(2,5-dimethoxyphenyl)pyridine, then the compounds prepared are 5-(3,4-dihydroxyphenyl)-2(1H)-pyridone (m.p. 307°–310° C.); 5-(3,4,5-trihydroxyphenyl)-2(1H)-pyridone (m.p. 300° C.) and 5-(2,5-dihydroxyphenyl)-pyridine (m.p. 216°–218° C.).

EXAMPLE 21

When the procedure of Example 17 is followed and 2-methoxy-5-[(2,5-dimethoxy-4-t-butyl)phenyl]pyridine is replaced by 2-methoxy-5-(6,7-dimethoxy-quinolin-3-yl)pyridine and the reaction is carried out at 160° C. for 5 minutes, then the product prepared is 5-(6,7-dimethoxyquinolin-3-yl)-2-(1H)pyridone (m.p. 259°–261° C.).

EXAMPLE 22

3-(6,7-dimethoxyquinolin-3-yl)pyridine

A solution of 600 mg (3.37 mmol) of methyl N-2-(pyrid-3-yl)vinylcarbamate in 10 mL of 6N H2SO4 is refluxed for 10 minutes, cooled to 0° C. and basified to pH 11 with 50% NaOH. A solution of 400 mg (2.03 mmol) of 2-amino-4,5-dimethoxybenzaldehyde is immediately added and the mixture refluxed for 2.5 hours, cooled to 22° C. and partitioned between ether (150 mL) and water (100 mL). The aqueous layer is back extracted with chloroform and the combined organics are dried (MgSO4) and evaporated to obtain an oil which is recrystallized from hexane/ethyl acetate twice to give 3-(6,7-dimethoxyquinolin-3-yl)pyridine (m.p. 131°–132° C.).

EXAMPLE 23

3-(indol-3-yl)-6,7-dimethoxyquinoline

A solution of 800 mg (5.03 mmol) of indol-3-yl-acetaldehyde (obtained from diisobutylaluminum hydride reduction of the ester and used immediately) and 800 mg (4.42 mmol) of 2-amino-4,5-dimethoxybenzaldehyde in 15 mL of ethanol is flushed thoroughly with nitrogen, treated with 0.5 mL of 1M NaOH and heated to 80° C. for 3 hours. The mixture is cooled to 22° C. and partitioned between chloroform (150 ml) and brine (100 mL). The organic layer is dried (MgSO4) and evaporated and the dark brown residue that results is chromatographed on silica gel (eluting with 97.5:2.5 chloroform/methanol). The product obtained is further chromatographed on silica gel (eluting with 98:2 ethyl acetate/methanol) and the resulting product is recrystallized from ethyl acetate to give 3-(indol-3-yl)-6,7-dimethoxyquinoline (m.p. 204°–206° C.).

EXAMPLE 24

When the procedure of Example 23 is followed and 2-amino-4,5-dimethoxybenzaldehyde is replaced with 2-aminobenzaldehyde, then the product prepared is 3-(indol-3-yl)quinoline (m.p. 173°–175° C.).

EXAMPLE 25

When the procedure of Example 23 is followed and indol-3-yl-acetaldehyde is replaced by phenylacetaldehyde then the product prepared is 3-phenyl-6,7-dimethoxyquinoline (m.p. 126.5°–128° C.)

EXAMPLE 26

6,7-dimethoxy-4-hydroxy-3-(thien-3-yl)-2(1H)-quinoline

A mixture of (0.632 g) 3,4-dimethoxyaniline, (1.00 g) diethyl thien-3-ylmalonate and (20 ml) diphenyl ether are heated at approximately 200° C. for 4 hours. The reaction mixture is extracted with 0.1N NaOH solution and the alkaline solution then acidified with 1N HCl and cooled in an ice water bath. The precipitate is collected, washed with ether and dried. The solid is then heated in EtOH, filtered and the filtrate evaporated in vacuo to give a light brown solid which is triturated with ether, filtered, and dried to give 6,7-dimethoxy-4-hydroxy-3-(thien-3-yl)-2(1H)-quinoline (m.p. 300° C. dec.).

EXAMPLE 27

2-(thien-2-yl)-4-carboxy-6,7-dimethoxyquinoline

To a boiling solution of 2-thiophenecarboxaldehyde (1.22 ml), pyruvic acid (0.904 ml) and 50 ml absolute EtOH is added dropwise a solution of 3,4-dimethoxyaniline (2.00 g) in 100 ml EtOH. The mixture is refluxed for approximately 4 hours, then stored at room temperature overnight. The greenish-yellow precipitate is collected by filtration, washed with fresh EtOH then with ether and allowed to air dry to obtain 2-(thien-2-yl)-4-carboxy-6,7-dimethoxyquinoline (m.p. 260°–263° C.).

EXAMPLE 28

When the procedure of Example 26 is followed and 2-thiophenecarboxaldehyde is replaced with 3-pyridinecarboxaldehyde or 2-imidazolcarboxaldehyde, then the products prepared are 2-(pyrid-3-yl)-4-carboxy-6,7-dimethoxyquinoline (m.p. 275° C. dec) and 2-(imidazol-2-yl)-4-carboxy-6,7-dimethoxyquinoline (m.p. 300° C. dec).

EXAMPLE 29

2-(N-phenylsulfonylindol-3-yl)-4-carboxy-6,7-dimethoxyquinoline

Pyruvic acid (0.486 ml) is added to a suspension of (2.00 g) of N-phenylsulfonyl-3-indolecarboxaldehyde in 100 ml absolute EtOH. The mixture is heated to reflux and a solution of 3,4-dimethoxyaniline (1.074 g) in 50 ml absolute EtOH is added dropwise. The reaction is then refluxed for approximately three hours and stirred at RT for 72 hours. The yellow precipitate is collected by filtration, washed with EtOH then with ether and the solid collected. This is triturated with EtOAC/EtOH and dried and used directly in the next step.

EXAMPLE 30

2-(indol-3-yl)-4-carboxy-6,7-dimethoxyquinoline

A stirred solution of (0.547 g) of 2-(N-phenylsulfonylindol-3-yl)-4-carboxy-6,7-dimethoxyquinoline, $K_2CO_3$ (0.380 g), MeOH (40 ml) and $H_2O$ (10 ml) are heated to reflux. The MeOH is evaporated in vacuo, and the aqueous residue diluted with more $H_2O$, and acidified with 0.1N HCl to pH between 6–7 while contained in an ice-bath. An orange solid precipitates. This is collected, washed with ether then dried under vacuum (0.1 mm at 22° C.) for a few hours to obtain 2-(indol-3-yl)-4-carboxy-6,7-dimethoxyquinoline (m.p. 286° C. dec).

EXAMPLE 31

3-cyclohexylethyl-6,7-dimethoxyquinoline

Step A 3-cyclohexylethynyl-6,7-dimethoxyquinoline

This reaction is carried out under anhydrous conditions. Cyclohexylacetylene (700 mg; 6.47 mmol) in 10 mL. THF is cooled to 0° C. To this is added 2.5M n-BuLi (3.0 mL; 7.44 mmol) and stirred for 30 min. at 0° C. under $N_2$ atm and then 1.0M $ZnCl_2$ (7.4 mL; 7.44 mmol). This is allowed to warm to room temperature and stirred for ¾ hour. The reaction mixture is transferred via cannula to a flask containing 6,7-dimethoxyquinolin-3-yl trifluoromethane sulfonate (500 mg; 1.48 mmol) and Pd(PPh₃)₄ (83 mg; 0.074 mmol)in 4 mL of THF. This is then heated to 50° C. under $N_2$ for 4½ hours. The reaction mixture is then poured into 90 mL of 10% $NH_4OH$, diluted with $CHCl_3$ and stirred for 20 min. The aqueous layer is separated, and the organic layer washed with brine, dried over $MgSO_4$, filtered, evaporated and chromatographed with 4:1 hexane: EtOAc to obtain 3-cyclohexylethynyl-6,7-dimethoxyquinoline, which is recrystallized from hexane, identified by NMR and used directly in the next step.

Step B 3-cyclohexylethyl-6,7-dimethoxyquinoline

To 3-cyclohexylethynyl-6,7-dimethoxyquinoline (215 mg; 0.73 mmol) in 10 mL $CH_3OH$ and 20 mL glacial acetic acid is added 22 mg 10% Pd/C. $H_2$ is bubbled through the reaction mixture and then filtered, evaporated to dryness and diluted with distilled water. This is then neutralized with $Na_2CO_3$, extracted with EtOAc, washed with brine, dried ($MgSO_4$), evaporated to dryness and chromatographed with 8:2/hexane: EtOAc to obtain 3-cyclohexylethyl-6,7-dimethoxyquinoline.

Calc'd: C: 76.22; H: 8.47; N: 4.69
Found: C: 75.08; H: 8.32; N: 4.59

EXAMPLE 32

3-benzyloxy-6,7-dimethoxyquinoline

To 3-hydroxy-6,7-dimethoxyquinoline (150 mg; 0.73 mmol) in 3 mL THF is added benzyl bromide (0.13 mL; 188 mg; 1.10 mmol) and NaH (59 mg; 1.46 mmol). This is stirred at room temperature for 1 hour and 25 mg of NaH added followed by 1,3-dimethyl-3,4,5,6-tetrahydro-2(1H)pyrimidinone (DMPU)(255 mg; 2.07 mmol) and stirred at room temperature for 3½ hours. The reaction mixture is partitioned between EtOAc and distilled $H_2O$ and extracted 2× with EtOAc. The latter is washed with brine, dried ($MgSO_4$), filtered, evaporated to dryness and chromatographed with 1% MeOH/$CHCl_3$ to obtain 3-benzyloxy-6,7-dimethoxyquinoline (m.p. 146.5°–148.5° C.).

EXAMPLE 33

The above examples may be followed to prepare any of the desired compounds of this invention. A representative list of compounds which may be prepared are shown below in Table VIII.

TABLE VIII 6-(thien-3-yl)-1,8-naphthyridin-2(1H)-one (m.p. 250°-250° C.)
3-(thien-3-yl)-6,7-dimethylquinoline (m.p. 132°-138° C.)
6-(4-methoxyphenyl)-1,8-naphthyridin-2(1H)-one (m.p. 251°-253° C.)
5,6-dimethoxy-2-(2-phenylethenyl)benzothiazole (m.p. 133°-135° C.)
3-(1-cyclopent-1-enyl)-6,7-dimethoxyquinoline hydrochloride (m.p. 213°-215° C.)
3-cyclopentyl-6,7-dimethoxyquinoline hydrochloride (m.p. 213.5°-215° C.)
4-(3-phenylpropyloxy)-6,7-dimethoxyquinoline (m.p. 90°-91.5° C.)
3-(thien-3-yl)-6,7-dimethoxy-2(1H)-quinolone (m.p. 264°-266° C.)
3-(thien-3-yl)-6,7-dimethoxyquinoline-N-oxide (m.p. 207°-208° C.)
3-(2-chlorothiophen-5-yl)-5,7-dimethoxyquinoline (m.p. 153°-154° C.)
3-(3-fluoro-4-methoxyphenyl)-6,7-dimethoxyquinoline (m.p. 165.5°-167° C.)
3-phenyl-4-carboxy-6,7-dimethoxyquinoline (m.p. 259°-262° C.)
3-(3-fluorophenyl)-6,7-dimethoxyquinoline (m.p. 156°-158° C.)
3-benzyl-5-(thien-3-yl)pyridine (m.p. 81°-82° C.)
4-(2-phenylethoxy)-6,7-dimethoxyquinoline (m.p. 117.5°-118.5° C.)
3-(4-methoxybenzyloxy)-6,7-dimethoxyquinoline (m.p. 115.5°-118° C.)
2-phenyl-6,7-dimethylquinoxaline (m.p. 128°-131° C.)
2-(4-methoxyphenyl)-6,7-dimethoxyquinoxaline hydrochloride (m.p. 212°-16° C.)
2-(thien-3-yl)-6,7-dimethoxyquinoxaline hydrochloride (m.p. 228°-231° C.)
2-(thien-3-yl)quinoxaline (m.p. 87.5°-89° C.)
2-phenyl-6,7-dimethoxyquinoxaline hydrochloride (m.p. 200° C.)
3-(thien-3-yl)-6,7-dimethoxyisoquinoline-N-oxide (m.p. 197°-200° C.)
3-(thien-3-yl)-6,7-dimethoxy-1(2H)-isoquinolone (m.p. 213°-216° C.)
4-(thien-3-yl)isoquinoline hydrochloride (m.p. 179°-183° C.)
4-(4-methoxyphenyl)isoquinoline hydrochloride (m.p. 196°-199° C.)
6,7-dimethyl-2-(thien-3-yl)-quinoxaline (m.p. 142°-143.5° C.)
4-(thien-3-yl)-6,7-dimethoxyquinazoline (m.p. 148.5°-151.5° C.)
4-benzyl-6,7-dimethoxyquinazoline (m.p. 122.5°-125° C.)
2-phenyl-6,7-diethoxyquinoxaline hydrochloride (m.p. 180°-185° C.)
2-(3-thienyl)-6,7-diethoxyquinoxaline hydrochloride (m.p. 217°-224° C.)
2-(5-chloro-2-thienyl)-6,7-diethoxyquinoxaline hydrochloride (m.p. 189°-194° C.)
2-(5-chloro-2-thienyl)-6,7-dimethoxyquinoxaline hydrochloride (m.p. 218°-25° C.)
3-(3-fluoro-4-methoxyphenyl)-7-fluoroquinoline (m.p. 138°-140.5° C.)
2-chloro-3-(thien-3-yl)-6,7-dimethoxyquinoline (m.p. 138.5°-139.5° C.)
2-methyl-3-(thien-3-yl)-6,7-dimethoxyquinoline (m.p. 132°-132.5° C.)
3-(thien-3-yl)-5-fluoroquinoline (m.p. 87.5°-89° C.)
2-(4-methylphenyl)-3-methyl-4(3H)quinazolinone (m.p. 139°-141° C.)
ethyl 4-(6,7-dimethoxyquinolin-3-yl)benzoate (m.p. 165°-166° C.)
4-phenylpropyl-6,7-dimethoxyquinoline hydrochloride (m.p. 144°-147° C.)
3-(thien-3-yl)-5,7-dimethylquinoline (m.p. 109.5°-111° C.)
3-(5-chlorothien-2-yl)-6,7-dimethylquinoline (m.p. 131.5°-132.5° C.)
3-(3-fluoro-4-methoxyphenyl)-7-methoxy-4(1H)-quinolone (m.p. 291°-293° C.)
3-(3-fluoro-4-methoxyphenyl)-5,7-dimethylquinoline (m.p. 109°-110° C.)
2-(4-methoxyphenyl)-6,7-dimethoxyquinoxaline-4-N-oxide (m.p. 224°-226° C.)
2-phenyl-6,7-dimethoxyquinoxaline-4-N-oxide (m.p. 219°-222° C.)
2-(4-methoxyphenyl)quinazolin-4(3H)-one (m.p. 244°-247° C.)
3-(thien-3-yl)-6,7-difluoroquinoline (m.p. 141.5°-143.5° C.)
3-(4-methoxyphyenyl)-7-methoxy-1-naphthalenol (m.p. 155°-159° C.)
2-phenyl-6,7-dimethoxy-4H-3,1-benzoxazin-4-one (m.p. 198°-201° C.)
2-(4-methoxyphenyl)-6,7-dimethoxyquinazolin-4(3H)-one (m.p. 288°-291° C.)
methyl 3-[3-(3-fluorophenyl)quinoline-6-yl]propenoate (m.p. 184°-186° C.)
ethyl 4-[3-(3-fluorophenyl)quinolin-6-yl]benzoate (m.p. 168°-170° C.)
3-benzyloxy-6,7-dimethoxyquinoline (m.p. 146.5°-148.5° C.)
3-(2-methoxypyrid-5-yl)-6,7-dimethoxyquinoline (m.p. 170.5°-171.5° C.)
3-cyclohexylethyl-6,7-dimethoxyquinoline (oil) (Calc'd/Fnd; C: 76.22/75.10; H: 8.42/8.30; N: 4.68/4.60)

PHARMACOLOGICAL TEST SECTION

Compounds within the scope of this invention have been subjected to various pharmacological tests as described below, the results of which are believed to correlate to useful cellular antiproliferative activity. The below described tests are useful in determining the EGF receptor kinase, PDGF receptor kinase and insulin receptor kinase inhibition activities of the compounds disclosed herein.

EGF-Receptor Purification

EGF-receptor purification is based on the procedure of Yarden and Schlessinger. A431 cells are grown in 80 cm² bottles to confluency ($2 \times 10^7$ cells per bottle). The cells are washed twice with PBS and harvested with PBS containing 11.0 mmol EDTA (1 hour at 37° C.), and centrifuged at 600 g for 10 minutes. The cells are solubilized in 1 ml per $2 \times 10^7$ cells of cold solubilization buffer (50 mmol Hepes buffer, pH 7.6, 1% Triton X-100, 150 mmol NaCl, 5 mmol EGTA, 1 mmol PMSF, 50 µg/ml aprotinin, 25 mmol benzamidine, 5 µg/ml leupeptic, and 10 µg/ml soybean trypsin inhibitor) for 20 minutes at 4° C. After centrifugation at 100,000 g for 30 minutes, the supernatant is loaded onto a WGA-agarose column (100 µl of packed resin per $2 \times 10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5M N-acetyl-D-glucosamine (200 μl per $2\times10^7$ cells.). The eluted material is stored in aliquots at $-70°$ C. and diluted before use with TMTNG buffer (50 mmol Tris-Mes buffer, pH 7.6, 0.1% Triton X-100, 150 mmol NaCl, 10% glycerol).

ATP and EGF Dependence of Autophosphorylation

WGA-purified EGF receptor from A431 cells (0.5 μg/assay is activated with EGF (0.85 μM) for 20 minutes at 4° C. The assay is performed at 15° C. and initiated by addition of Mg(Ac)$_2$ (60 mmol), Tris-Mes buffer, pH 7.6 (50 mmol), [$^{32}$P]ATP (carder free, 5 μCi/assay), and increasing concentrations of nonradioactive ATP. The assay is terminated after 10-sec by addition of SDS sample buffer. The samples are run on a 6% SDS polyacrylamide gel. The gel is dried and autoradiographed as described above. The relevant radioactive bands are cut and counted in the Cerenkov mode. The K$_m$ for ATP determined in this fashion is found to be 7.2 μM. With use of the 10-sec assay protocol, the EGF concentration dependence of EGF-RK autophosphorylation is determined.

Inhibition of EGF-R Autophosphorylation

A431 cells were grown to confluence on human fibronectin coated tissue culture dishes. After washing 2 times with ice-cold PBS, cells were lysed by the addition of 500 μl/dish of lysis buffer (50 mmol Hepes, pH 7.5, 150 mmol NaCl, 1.5 mmol MgCl$_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 μg/ml 10 minutes at 37° C.) immunoprecipitation was performed with anti EGF-R (Ab 108) and the autophosphorylation reaction (50 μl aliquots, 3 μCi [γ-$^{32}$P]ATP) sample was carried out in the presence of 2 or 10 μM of compound of the present invention, for 2 minutes at 4° C. The reaction was stopped by adding hot electrophoresis sample buffer. SDA-PAGE analysis (7.5% els) was followed by autoradiography and the reaction was quantitated by densitometry scanning of the x-ray films.

In order to test the present compounds for selective inhibition, the procedure is repeated using PDGF stimulation in place of EGF stimulation. "IC$_{50}$," as used below refers to the concentration of inhibitor (μM) at which the rate of autophosphorylation is halved, compared with media containing no inhibitor.

Inhibition of PDGF-R Autophosphorylation

Lysate from NIH 3T3 cells was diluted one-third in Triton-free buffer and stimulated with 10 ng/ml PDGF for 30 minutes at 4° C. The equivalent of 1/15 of a 175-cm$^2$ plate of lysate was used per sample. The stimulated lysate was then immunoprecipitated with rabbit polyclonal anti-PDGF-receptor antibodies raised against a synthetic peptide from the COOH-terminal region (amino acids 1094–1106) or the human PDGF-receptor β-subunit and added to increasing concentrations of test compound of the present invention. After 10 minutes at 4° C., 10 μCi of [γ-$^{32}$P]ATP were added and further incubated for 10 minutes at 4° C. Samples were separated by SDS-PAGE on 6% gels.

Inhibition of Cell Proliferation as Measured by Inhibition of DNA Synthesis

EGF receptor overexpressing (HER14) cells were seeded at $1\times10^5$ cells per well in 24-well Costar dishes pre-coated with human fibronectin (by incubating for 30 minutes at room temperature with 10 μg/0.5 ml/well). The cells were grown to confluence for 2 days. The medium was changed to DMEM containing 0.5 calf serum for 36–48 hours and the cells were then incubated with EGF (Toyobo, New York, N.Y.) (20 ng/ml), PDGF (Amgen) (20 ng/ml) or serum (10% calf serum, FCS) and different concentrations of the compound of the present invention. [$^3$H] thymidine, (NEN, Boston, Mass.) was added 16–24 hours later at 0.51 μCi/ml for 2 hours. TCA precipitable material was quantitated by scintillation counting (C) Results of this assay are determined. "IC$_{50}$" of the concentration of inhibitor (nM) at which [$^3$H]thymidine incorporation is halved, compared with media containing no buffer is calculated As FCS contains a broad range of growth factors, the IC$_{50}$ values for PDGF should be lower than for FCS, indicating that the compounds of the present invention do not act as general inhibitors.

These results indicate that compounds within the scope of the invention inhibit the EGF and/or PDGF growth factor receptors selectively.

Cell Culture

Cells termed HER 14 and K721A (=DK) were prepared by transfecting NIH3T3 cells (clone 2.2) (From C. Fryling, NCl, NIH), which lack endogenous EGF-receptors, with cDNA constructs of wild-type EGF-receptor or mutant EGF-receptor lacking tyrosine kinase activity (in which Lys 721 at the ATP-binding site was replace by an Ala residue, respectively). All cells were grown in DMEM with 10% calf serum (Hyclone, Logan, Utah).

The results obtained by the above experimental methods evidence the useful protein tyrosine kinase inhibition properties of compounds within the scope of the present invention. The following table shows examples of representative compounds of this invention and their test results as determined by the above inhibition of PDGF-R cell-free autophosphorylation procedure.

| COMPOUND | Inhibition of PDGF-R cell-free Autophosphorylation IC$_{50}$ (μM) |
|---|---|
| (quinoline with MeO, MeO substituents and 4-OMe-phenyl group) | 0.003–0.015 |
| (quinoline with MeO, MeO substituents and thiophene group) | 0.050–0.10 |

-continued
| COMPOUND | Inhibition of PDGF-R cell-free Autophosphorylation IC$_{50}$ (μM) |
|---|---|
| 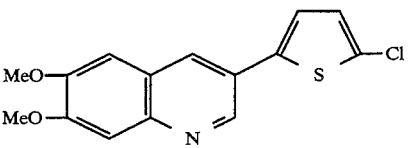 | 0.007 |
| 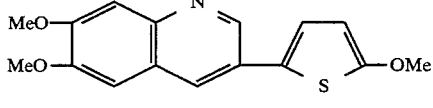 | 0.2–1 |
| 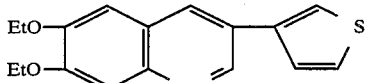 | 0.06–0.08 |
| 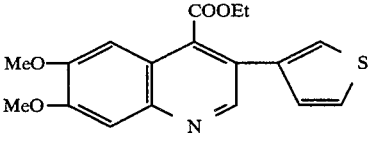 | 1.0–2.0 |
| 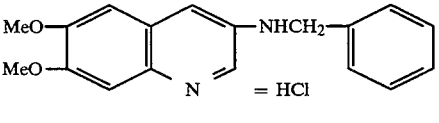 | 0.02–0.08 |
| 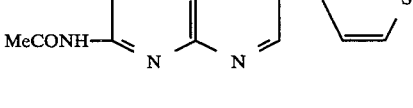 | 0.05–0.1 |
| 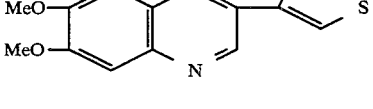 | 0.005–0.030 |
| 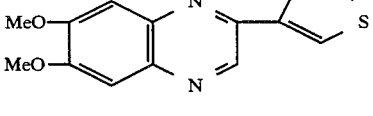 | 0.02–0.05 |
| 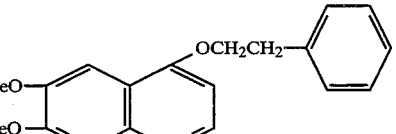 | 0.7–1.0 |
| 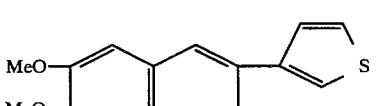 | 0.7–1.0 |
-continued
| COMPOUND | Inhibition of PDGF-R cell-free Autophosphorylation IC$_{50}$ (μM) |
|---|---|
| 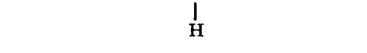 | 0.04 |
| 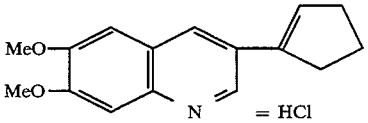 | 0.010–0.060 |
| 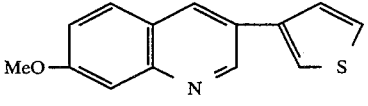 | 7–12 |
| 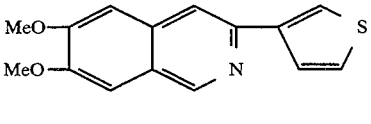 | 0.015 |
| 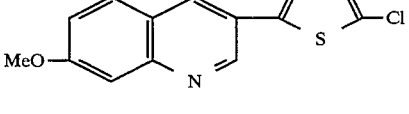 | 15–20 |
| 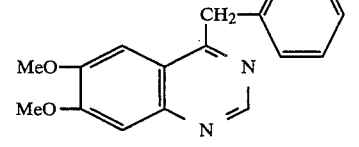 | 0.005–0.030 |
| 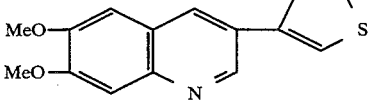 | 0.02–0.05 |
| 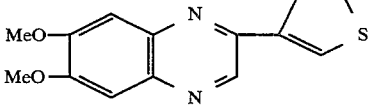 | 0.7–1.0 |
| 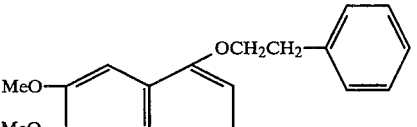 | 0.7–1.0 |
| 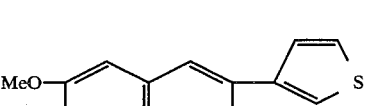 | 0.04 |

| COMPOUND | Inhibition of PDGF-R cell-free Autophosphorylation IC$_{50}$ ($\mu$M) |
|---|---|
| MeO-[quinoline]-thiophene | 0.010–0.060 |
| MeO-MeO-[isoquinoline]-thiophene | 7–12 |
| OMe, MeO-[quinoline]-thiophene-Cl | 0.015 |
| MeO-MeO-[quinazoline with CH$_2$-phenyl] | 15–20 |
| MeO-MeO-[quinoline]-thiophene · HCl | 0.02 |
| MeO-MeO-[quinoline]-phenyl-N$_3$ | 0.01 |
| MeO-MeO-[quinoxaline]-[pyridine]-OMe | 0.030–0.070 |

We claim:

1. A compound selected from the group consisting of:
3-(thien-3-yl)-6,7-dimethoxyquinoline;
3-(thien-3-yl)-7-methoxyquinoline;
3-(4-methoxyphenyl)-6,7-dimethoxyquinoline;
3-(5-chlorothien-2-yl)-6,7-dimethoxyquinoline;
3-(3-fluoro-4-methoxyphenyl)-6,7-dimethoxyquinoline;
3-(2-chlorothien-2-yl)-5,7-dimethoxyquinoline;
3-(thien-3-yl)-6,7-dimethylquinoline;
3-(1-cyclopent-1-enyl)-6,7-dimethoxyquinoline;
3-cyclopentyl-6,7-dimethoxyquinoline;
4-(3-phenylpropyloxy)-6,7-dimethoxyquinoline;
3-(thien-3-yl)-6,7-dimethoxyquinoline-N-oxide;
3-(2-chlorothien-5-yl)-5,7-dimethoxyquinoline;
3-(3-fluoro-4-methoxyphenyl)-6,7-dimethoxyquinoline;
3-(3-fluorophenyl)-6,7-dimethoxyquinoline;
4-(2-phenylethoxy)-6,7-dimethoxyquinoline;
3-(4-methoxybenzyloxy)-6,7-dimethoxyquinoline;
2-(4-methoxyphenyl)-6,7-dimethoxyquinoxaline;
2-(thien-3-yl)-6,7-dimethoxyquinoxaline;
2-phenyl-6,7-dimethoxyquinoxaline;
6,7-dimethyl-2-(thien-3-yl)-quinoxaline;
2-phenyl-6,7-diethoxyquinoxaline;
2-(3-thienyl)-6,7-diethoxyquinoxaline;
2-(5-chloro-2-thienyl)-6,7-diethoxyquinoxaline;
2-(5-chloro-2-thienyl)-6,7-dimethoxyquinoxaline;
3-(3-fluoro-4-methoxyphenyl)-7-fluoroquinoline;
3-(thien-3-yl)-5,7-dimethylquinoline;
3-(5-chlorothien-2-yl)-6,7-dimethylquinoline;
3-(thien-3-yl)-6,7-difluoroquinoline or
3-(4-methoxyphyenyl)-7-methoxy-1-naphthalenol.

2. A pharmaceutical composition wherein the active ingredient is selected from the compounds of claim 1.

3. A compound according to claim 1 selected from
3-(thien-3-yl)-6,7-dimethoxyquinoline;
3-(thien-3-yl)-6,7-dimethoxyquinoline-N-oxide;
3-(thien-3-yl)-6,7-dimethylquinoline;
3-(thien-3-yl)-6,7-difluoroquinoline;
3-(thien-3-yl)-5,7-dimethylquinoline; or
3-(thien-3-yl)-7-methoxyquinoline.

4. A compound according to claim 1 selected from
3-(2-chlorothien-5-yl)-6,7-dimethoxyquinoline;
3-(2-chlorothien-5-yl)-5,7-dimethoxyquinoline; or
3-(2-chlorothien-5-yl)-6,7-dimethylquinoline.

5. A compound according to claim 1 selected from
3-(4-methoxyphenyl)-6,7-dimethoxyquinoline;
3-(3-fluorophenyl)-6,7-dimethoxyquinoline; or
3-(3-fluoro-4-methoxyphenyl)-6,7-dimethoxyquinoline.

6. A compound according to claim 1 which is 3-(3-fluoro-4-methoxyphenyl)-7-fluoroquinoline.

7. A compound according to claim 1 selected from
3-(1-cyclopent-1-enyl)-6,7-dimethoxyquinoline; or
3-cyclopentyl-6,7-dimethoxyquinoline.

8. A compound according to claim 1 selected from
4-(3-phenylpropyloxy)-6,7-dimethoxyquinoline; or
4-(2-phenylethoxy)-6,7-dimethoxyquinoline.

9. A compound according to claim 1 which is 3-(4-methoxybenzyloxy)-6,7-dimethoxyquinoline.

10. A compound according to claim 1 selected from
2-phenyl-6,7-dimethoxyquinoxaline;
2-phenyl-6,7-diethoxyquinoxaline; or
2-(4-methoxyphenyl)-6,7-dimethoxyquinoxaline.

11. A compound according to claim 1 selected from
2-(5-chlorothien-2-yl)-6,7-diethoxyquinoxaline; or
2-(5-chlorothien-2-yl)-6,7-dimethoxyquinoxaline.

12. A compound according to claim 1 selected from
2-(thien-3-yl)-6,7-dimethoxyquinoxaline;
2-(thien-3-yl)-6,7-diethoxyquinoxaline; or
2-(thien-3-yl)-6,7-dimethylquinoxaline.

13. A compound according to claim 1 which is 3-(4-methoxyphenyl)-7-methoxy-1-naphthalenol.

* * * * *